United States Patent [19]

Belef

[11] Patent Number: 5,503,154

[45] Date of Patent: Apr. 2, 1996

[54] TRANSDUCER FOR INTRALUMINAL ULTRASOUND IMAGING CATHETER WITH PROVISION FOR ELECTRICAL ISOLATION OF TRANSDUCER FROM THE CATHETER CORE

[75] Inventor: William M. Belef, San Jose, Calif.

[73] Assignee: Cardiovascular Imaging Systems, Inc., Sunnyvale, Calif.

[21] Appl. No.: 322,857

[22] Filed: Oct. 13, 1994

[51] Int. Cl.⁶ ..................................................... A61B 8/12
[52] U.S. Cl. ..................................................... 128/662.03
[58] Field of Search ................ 128/660.01, 662.03, 128/662.06, 663.01; 310/334, 357, 358, 365, 366

[56] References Cited

U.S. PATENT DOCUMENTS

| 5,000,185 | 3/1991 | Yock | 128/662.03 |
| 5,295,487 | 3/1994 | Saitoh et al. | 128/662.03 |
| 5,353,798 | 10/1994 | Sieben | 128/662.03 |

Primary Examiner—George Manuel
Attorney, Agent, or Firm—Townsend and Townsend and Crew

[57] ABSTRACT

An improved electrical interconnection system for an ultrasonic transducer included in an intraluminal catheter is electrically isolated from the imaging core and provides for a balanced transmission line to improve noise rejection.

4 Claims, 5 Drawing Sheets

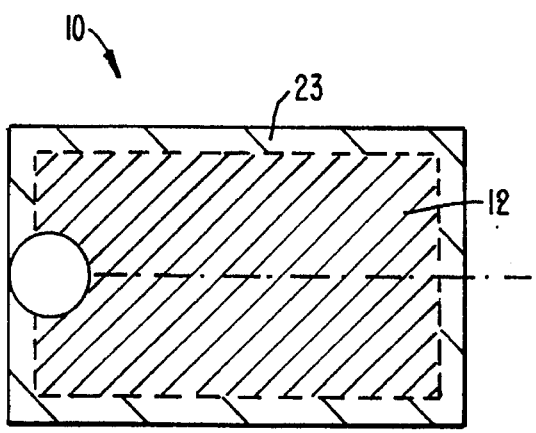
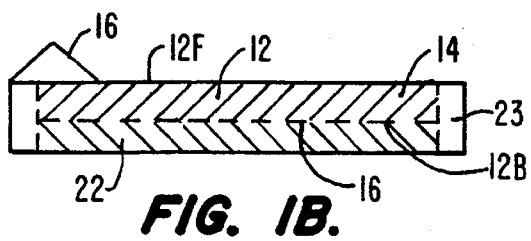
FIG. 1A.
FIG. 1B.
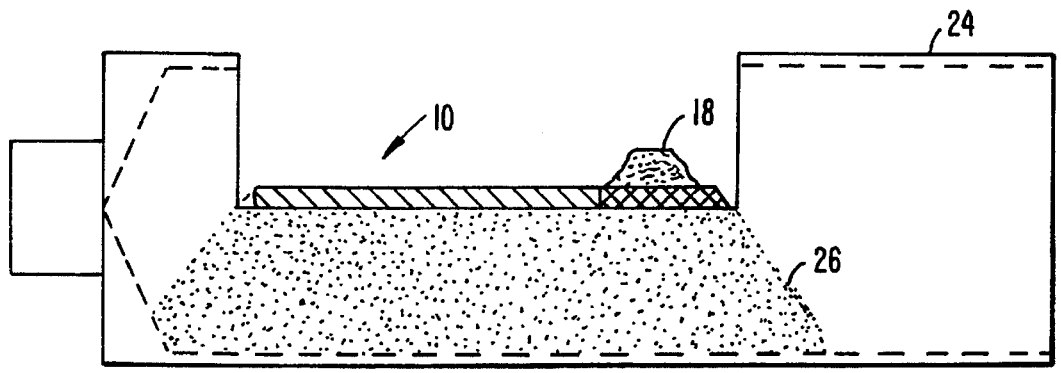
FIG. 2.
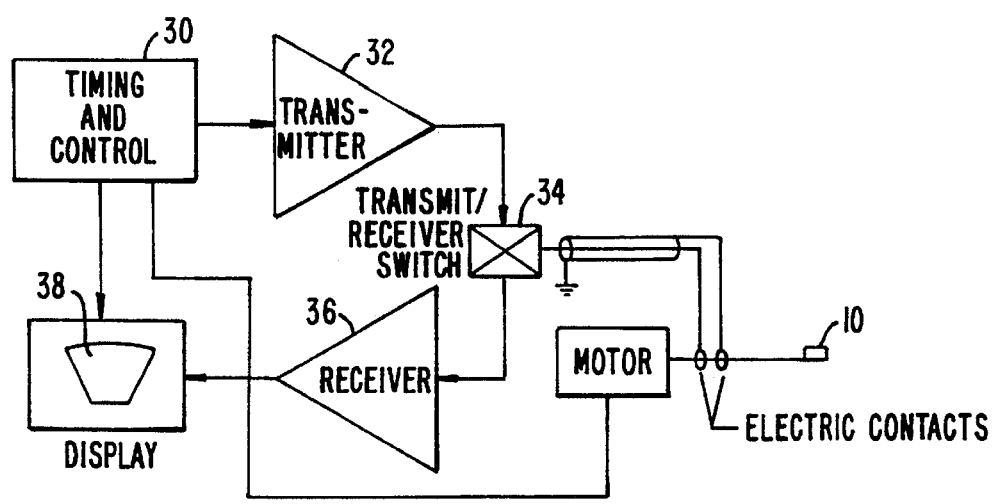
FIG. 3.

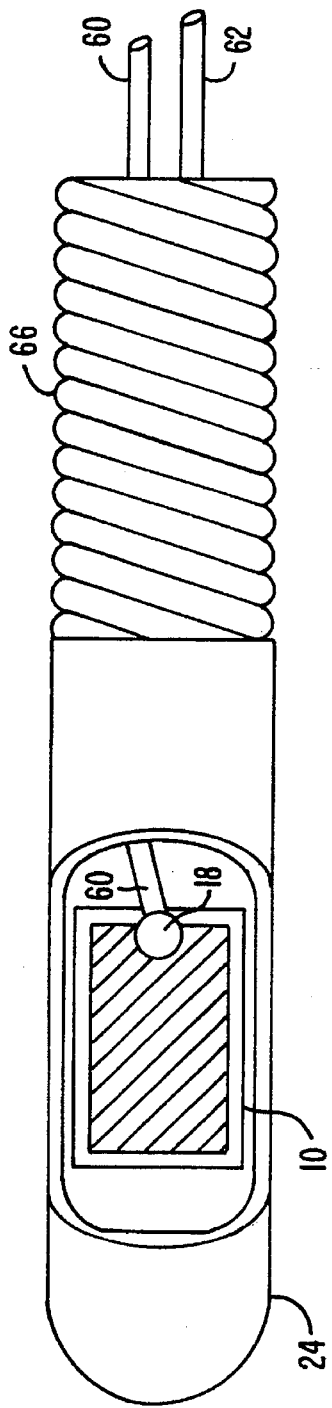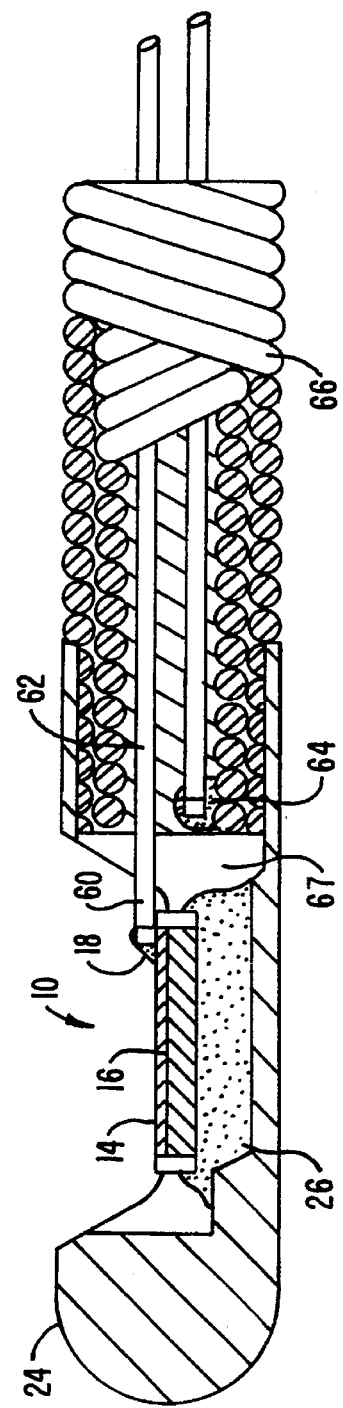

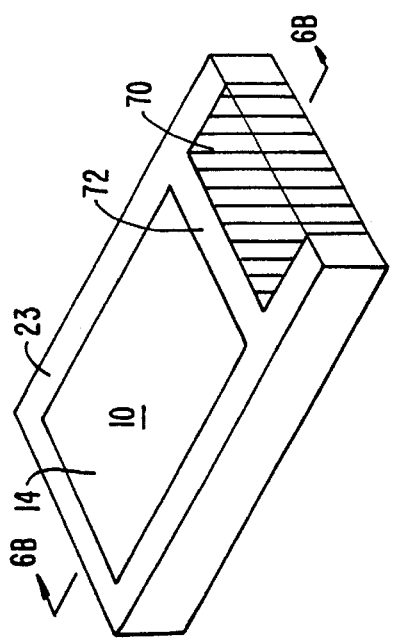
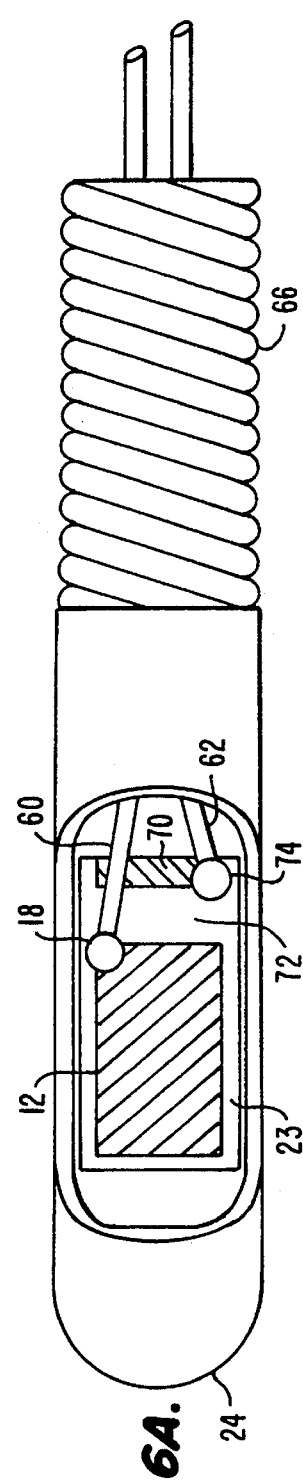
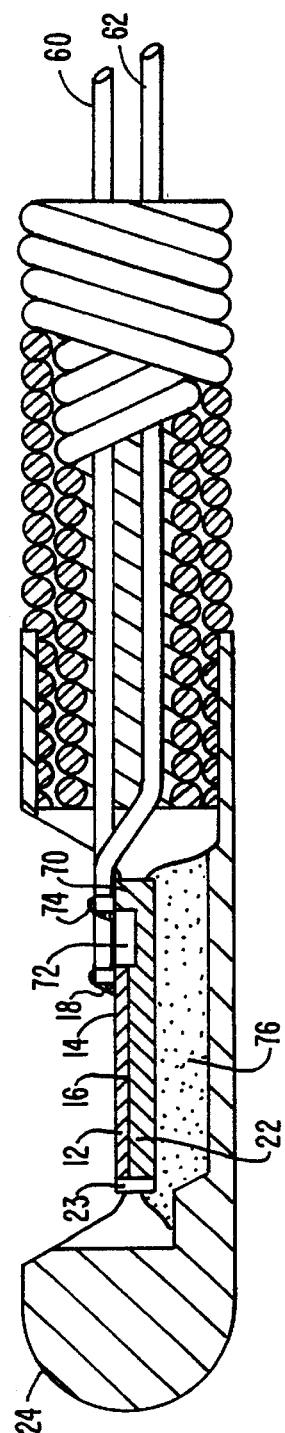
FIG. 5.
FIG. 6A.
FIG. 6B.

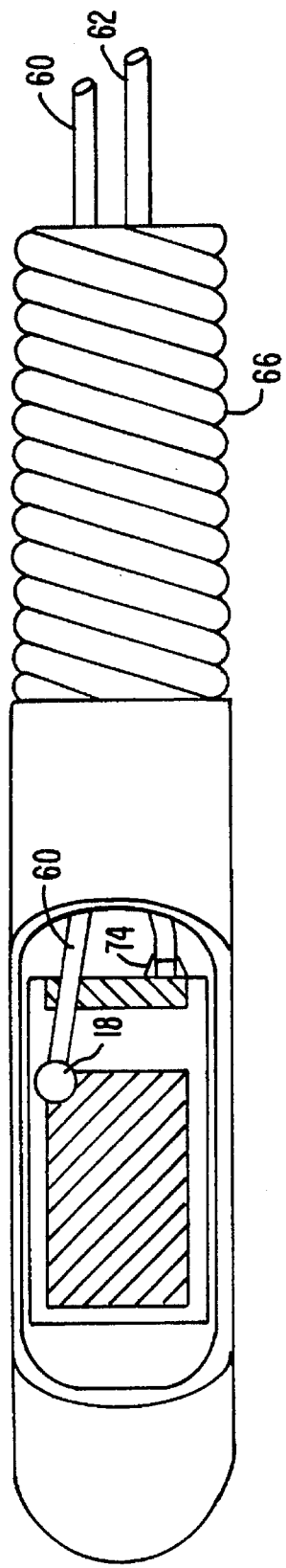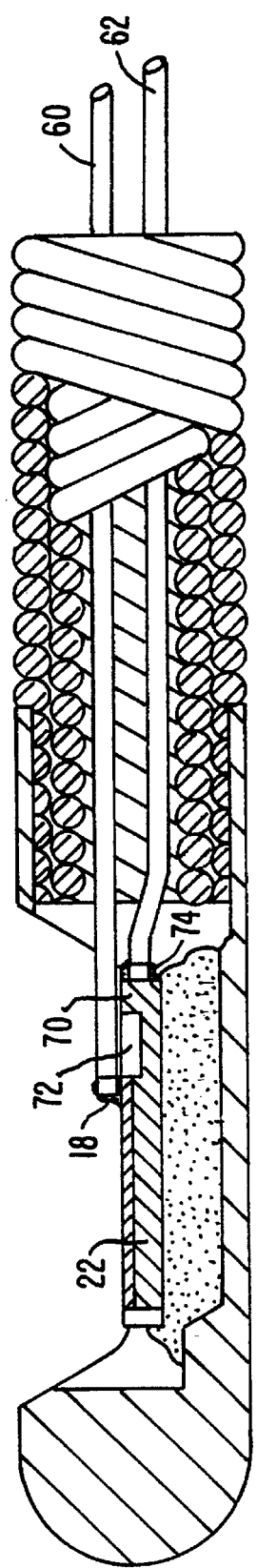

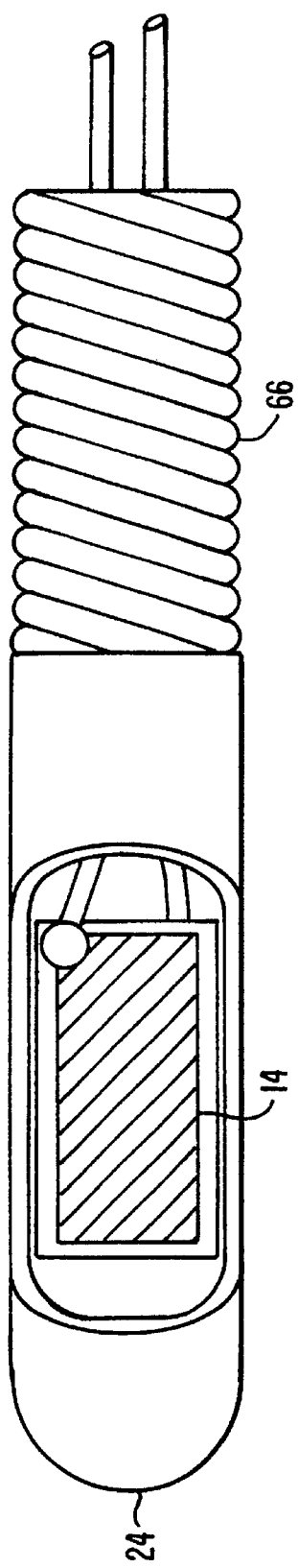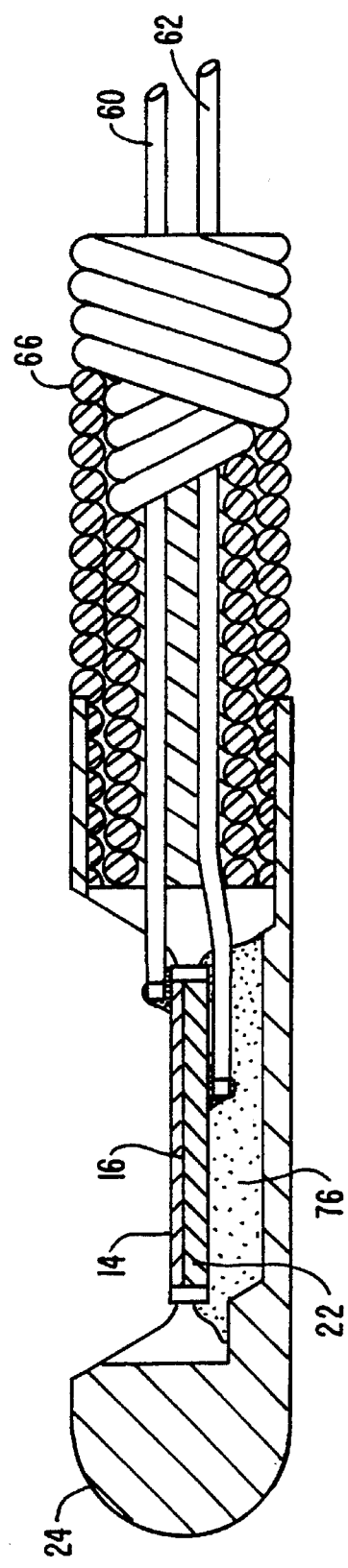

5,503,154

TRANSDUCER FOR INTRALUMINAL ULTRASOUND IMAGING CATHETER WITH PROVISION FOR ELECTRICAL ISOLATION OF TRANSDUCER FROM THE CATHETER CORE

BACKGROUND OF THE INVENTION

The invention relates to an ultrasonic transducer for use in a catheter apparatus and more particularly to such a transducer having an electrical connection configuration providing for optimum performance and noise rejection.

Catheters utilizing ultrasonic transducers for performing intraluminal ultrasonic imaging are known in the art. Typically, the transducer generates a high-frequency electrical signal, on the order of 30 MHz, which is utilized to generate an image.

The quality of an image is degraded by radio frequency noise which may be mixed with the signal. A typical hospital environment has many sources of noise, e.g., patient monitoring systems, intra aortic balloon pumps, x-ray systems, and computer components. These sources of noise may be coupled to a transducer generated signal by the conductors utilized to transmit the signal from the transducer to the image generating system.

Since the quality of the image generated by the system is increased when noise is reduced there is a critical need for improved technology to reduce the noise generated spurious RF signals present in the operating room.

SUMMARY OF THE INVENTION

The present invention is an improved system for transmitting an RF signal from an ultrasonic transducer in an intraluminal catheter to an image generating system.

According to one aspect of the invention, a balanced transmission line, isolated from the distal housing and drive cable, transmits high frequency electrical signals from an ultrasonic transducer utilized to perform medical ultrasonic imaging.

According to another aspect of the invention, an active transducer element has top and bottom major surfaces with top and bottom electrodes formed thereon. A conductive backing element is coupled to the bottom electrode and a backing extension element, extending toward the top major surface, is electrically coupled to the backing element with an insulating member electrically isolating the backing extension element from the top electrode.

According to another aspect of the invention, the backing element is connected to a distal housing by a non-conducting adhesive. First and second leads are coupled, respectively, to the top electrode and backing extension element to form a balanced transmission line to facilitate noise rejection and optimal performance.

Other advantages and features of the invention will become apparent in view of the following detailed description and appended drawings.

BRIEF DESCRIPTION OF THE DRAWINGS

FIGS. 1A and 1B are top and cross-sectional views, respectively, of a standard transducer;

FIG. 2 is a cross-sectional view of a standard transducer mounted in a distal housing;

FIG. 3 is a schematic view of a standard system for energizing the transducer;

FIGS. 4A and 4B are top and cross-sectional views, respectively, of the electrical connection to the standard transducer mounted in the distal housing;

FIG. 5 is a perspective view of a preferred embodiment of the invention;

FIGS. 6A and 6B are top and cross-sectional views, respectively, of the electrical connection to the transducer depicted in FIG. 5 mounted in the distal housing;

FIGS. 7A and 7B are top and cross-sectional views, respectively, of the electrical connections to a transducer in a second preferred embodiment of the invention; and FIGS. 8A and 8B are top and cross-sectional views, respectively, of the electrical connections to a transducer in a third preferred embodiment of the invention.

DESCRIPTION OF THE PREFERRED EMBODIMENTS

FIGS. 1A and 1B are schematic diagrams depicting an ultrasonic transducer system for emitting and detecting pulses of ultrasonic energy; FIG. 2 is a schematic diagram of the transducer mounted in a distal housing of a catheter; and FIG. 3 is a schematic diagram of a typical system for exciting the transducer to emit an ultrasonic pulse and to detect a received ultrasonic pulse.

Turning first to FIGS. 1A and 1B, the ultrasonic transducer 10 includes an active transducer element 12 which is part of an assembly. The function of the active transducer element 12 is to convert ultrasonic pulses to electric pulses and electric pulses to ultrasonic pulses. The transducer element 12 is fabricated from PZT ceramic material, has a block-like configuration, and includes front and back opposing major surfaces 12F and 12B. These major surfaces 12F and 12B are covered by metallic conducting films, formed of a suitable material such as chrome or gold, which function as top and bottom electrodes 14 and 16. The material of the films can be formed of a foil or can be in the form of films evaporated or sputtered onto the opposing surfaces of the transducer element 12. The top electrode 14 has a silver epoxy dot 18 disposed thereon to be connected to a wire. The transducer element 12 may have a ¼-wave impedance matching layer on the front surface which is not shown in the figure.

A backing element 22 of a suitable backing material is bonded to the back surface of the transducer element 12 to attenuate ultrasonic energy emitted by the back fate 12B of the transducer element 12. The backing element 22 has a front surface 22F bonded to the back surface 12B of the transducer element 12. An insulating layer 23 surrounds the perimeter of the transducer element 12 and backing 22.

FIG. 2 depicts a transducer 10 mounted in a distal housing 24. The transducer element 12 is mounted on a bed 26 of adhesive filler material, such as silver epoxy, and the back surface 22B of the backing element 22 is in contact with the bed 26. Typically, the backing element 22 and the bed 26 are fabricated of electrically conductive materials and function as a conductive path forming the electrical contact to the bottom electrode 16.

Turning now to FIG. 3, a typical system for energizing the transducer 10 to emit ultrasonic pulses and for detecting received pulses is depicted. This system is not part of the invention and will be described only briefly. A timing and control block 30 controls a transmitter 32 to emit a series of voltage pulses of a predetermined duration separated by a predetermined intervals. The switch 34 couples the transmitter 32 to the transducer 10 when the pulses are generated and couples a receiver 36 to the transducer 10 during the intervals between pulses.

The received pulses are processed by an image generating system 38 which is not part of the invention. The primary information utilized to generate an image is the delay time between the transmission of an ultrasonic pulse and the receipt of the received pulse. Other information such as the amplitude and phase of the received pulse can also be processed.

As is well-known, when a voltage pulse is applied to the electrodes 14 and 16 the transducer element 12 oscillates to generate a pulse centered on a resonant frequency determined by the mechanical and piezoelectric properties of the transducer 10. Thus, a series of ultrasonic pulses separated by the predetermined interval is transmitted.

Conversely, when an ultrasonic pulse is received by the transducer 10 an imaging signal, in the form a voltage pulse, is generated on the electrodes 14 and 16 which is amplified by the receiver 36 and transmitted to the image generating system 38. The pulse is typically a very high frequency pulse, on the order of 30 MHz, which is transmitted through a pair of conductors routed through the catheter to the amplifier.

The electrical connection of leads to the transducer depicted in FIG. 2 is depicted in FIGS. 4A and 4B. A first lead 60 is connected to the silver epoxy dot 18 disposed on the upper electrode and a second lead 62 is electrically coupled to the second electrode. The electrical coupling of the second lead 62 to the bottom electrode follows a path from the second lead 62 through a conductive adhesive 64 coupling the lead to a drive cable 66, through a weld to the distal housing 24, and from the distal housing 24 to the bottom electrode through the conductive acoustic backing 22. The electrical leads 60 and 62 run the length of the catheter imaging core.

While the above-described electrical path from the second lead to the bottom electrode is adequate for electrical connection alone, it creates an impedance imbalance of the catheter transmission line. The first lead 60 is connected to only the active transducer element 12 while the second lead 62 is connected to not only the active transducer element 22, but is also connected through the conductive adhesive 26 to distal housing 24 and drive cable 66 of the imaging core. Thus, the different terminal impedances of the first and second leads 60 and 62 result in an imbalanced transmission line. This imbalance results in a greatly reduced ability of the catheter to reject RF noise from external sources.

Additional, the inventors have discovered that the drive cable 66 acts as an antenna to receive spurious rf noise signals generated in an operating room environment. These received noise signals are mixed with the imaging signal generated by the transducer 10 because the second lead 62 is electrically coupled to the drive cable 66. Thus, the electrical isolation of the leads 60 and 62 from the drive cable 66 reduces the mixing of spurious rf signals with the imaging signal.

The configuration of the electrical connection mechanism of a preferred embodiment of the invention will now be described with reference to FIGS. 5, 6A, and 6B. FIG. 5 is a perspective view, FIG. 6A is a top view, and FIG. 6B is a cross-sectional view taken along line 6B'—6B' of FIG. 5. Referring now to those figures, the conductive backing element 22 has an extension part 70 which extends to the top surface of transducer assembly 10. This extension element is electrically isolated from the top electrode by an insulating strip 72. As can be seen from FIG. 5, the combination of the insulating layer 23 surrounding the perimeter of the active element and backing and insulating strip 72 electrically isolates the top electrode 14 from the backing element/extension 22/70. As depicted in FIG. 6B, the insulating strip 72 does not extend through the backing element so that a conductive path from the extension 70 to the bottom electrode 16 of the active element 10 is formed.

Thus, as depicted in FIGS. 6A and B, both leads 60 and 62 are connected to the top surface of the assembly 10. The second lead 62 is coupled via a second silver dot 74 to the extension 70. A non-conducting adhesive 76 is utilized as an acoustic backing and mounting technique to connect the transducer assembly 10 to the distal housing 24. Accordingly, the second lead 62 is electrically isolated from the housing 24 and the drive cable 66 to provide a balanced transmission line.

FIGS. 7A and B and 8A and B depict alternative embodiments for providing a balanced transmission line and for isolating noise received by the drive cable from the imaging signal.

In the embodiment depicted in FIGS. 7A and B the second lead 64 is coupled to the back of the extension 70 by the second silver epoxy dot 74.

In the embodiment depicted in FIGS. 8A and B there is no backing extension 70 or insulating strip 72. The second lead 62 is coupled to the backing element 22 at the bottom of the transducer 10 and is insulated from the housing 24 and drive cable 66 by the non-conducting adhesive 76.

The second cable 62 can be connected prior to mounting the transducer 10 with the non-conducting adhesive 76 or subsequent to mounting by drilling a hole in the non-conducting adhesive 76.

The invention has now been described with reference to the preferred embodiments. Alternatives and substitutions will now be apparent to persons of skill in the art. Accordingly, it is not intended to limit the invention except as provided by the appended claims.

What is claimed is:

1. An ultrasonic transducer assembly for use in a catheter for performing ultrasonic imaging in the body of a patient, said transducer assembly comprising:

an active transducer element, having top and bottom major surfaces and a perimeter, for performing transformations between electrical and ultrasonic signals;

a top electrode formed on said top major surface;

a bottom electrode formed on said bottom major surface;

a conductive backing element, having top and bottom major surfaces and a perimeter of substantially the same shape as the perimeter of said active transducer element, having its top major surface electrically coupled to said bottom electrode;

a conductive backing extension element, electrically coupled to said backing element and extending toward the top major surface of said active transducer element; and an insulating member electrically insulating said backing extension element from said top electrode.

2. An ultrasonic transducer assembly for use in a catheter for performing ultrasonic imaging in the body of a patient, said transducer assembly comprising:

an active transducer element, having top and bottom major surfaces and a perimeter, for performing transformations between electrical and ultrasonic signals;

a top electrode formed on said top major surface;

a bottom electrode formed on said bottom major surface;

a conductive backing element, having top and bottom major surfaces and a perimeter of substantially the same shape as the perimeter of said active transducer element, having its top major surface electrically coupled to said bottom electrode;

a conductive backing extension element, electrically coupled to said backing element, having a top surface substantially coplanar with the top major surface of said active transducer element and a bottom surface substantially coplanar with the bottom surface of said conductive backing element; and an insulating member electrically insulating said backing extension element and said backing element from said top electrode.

3. An electrical interconnection system for forming a balanced transmission line for transmitting high-frequency electrical signals generated by an electronic transducer assembly included in a catheter for insertion into the body of a patient, said system comprising:

a transducer assembly including:
an active transducer element, having top and bottom major surfaces and a perimeter, for performing transformations between electrical and ultrasonic signals;
a top electrode formed on said top major surface;
a bottom electrode formed on said bottom major surface;
a conductive backing element, having top and bottom major surfaces and a perimeter of substantially the same shape as the perimeter of said active transducer element, having its top major surface electrically coupled to said bottom electrode;
a conductive backing extension element, electrically coupled to said backing element and extending toward the top major surface of said active transducer element; and
an insulating member electrically insulating said backing extension element from said top electrode;

a distal housing of the catheter having a transducer mounting cavity formed therein with said transducer assembly mounted in said cavity and electrically isolated from said cavity;

a first lead electrically coupled to said top electrode and electrically isolated from the catheter; and a second lead electrically coupled to the backing extension element and electrically isolated from the catheter so that said second lead is electrically isolated form the distal housing and said first and second leads form a balanced transmission line.

4. An electrical interconnection system, for use in a catheter, for forming a balanced transmission line for transmitting high-frequency electrical signals coupled to an electronic transducer assembly included in an imaging core including a distal housing and drive cable for insertion into the body of a patient, said system comprising:

a transducer assembly including:
an active transducer element, having top and bottom major surfaces and a perimeter, for performing transformations between electrical and ultrasonic signals;
a top electrode formed on said top major surface;

a bottom electrode formed on said bottom major surface;
a conductive backing element, having top and bottom major surfaces and a perimeter of substantially the same shape as the perimeter of said active transducer element, having its top major surface electrically coupled to said bottom electrode;

a distal housing of the catheter having a transducer mounting cavity formed therein with said transducer assembly mounted in said cavity and electrically isolated from said cavity and the drive cable;

a first lead electrically coupled to said top electrode and electrically isolated from the imaging core; and a second lead electrically coupled to the conductive backing element so that said second lead is electrically isolated form the imaging core and said first and second leads form a balanced transmission line.

* * * * *